US008062904B2

(12) United States Patent
Gauer

(10) Patent No.: US 8,062,904 B2
(45) Date of Patent: Nov. 22, 2011

(54) METHOD AND DEVICE FOR DOSING AND MIXING SMALL AMOUNTS OF LIQUID

(75) Inventor: Christoph Gauer, Munich (DE)

(73) Assignee: Beckman Coulter, Inc., Brea, CA (US)

( * ) Notice: Subject to any disclaimer, the term of this patent is extended or adjusted under 35 U.S.C. 154(b) by 563 days.

(21) Appl. No.: 11/794,768

(22) PCT Filed: Dec. 16, 2005

(86) PCT No.: PCT/EP2005/013597
§ 371 (c)(1),
(2), (4) Date: Mar. 5, 2009

(87) PCT Pub. No.: WO2006/072383
PCT Pub. Date: Jul. 13, 2006

(65) Prior Publication Data

US 2011/0045595 A1 Feb. 24, 2011

(30) Foreign Application Priority Data

Jan. 5, 2005 (DE) ......................... 10 2005 000 834
Jan. 5, 2005 (DE) ......................... 10 2005 000 835

(51) Int. Cl.
*G01N 1/20* (2006.01)
*G01N 1/38* (2006.01)
*G01N 33/00* (2006.01)

(52) U.S. Cl. ......... 436/180; 436/174; 422/63; 422/68.1; 422/502; 422/504; 422/507; 422/509; 366/127; 366/348

(58) Field of Classification Search .................... 436/43, 436/174, 180; 422/67, 502, 503, 504, 507, 422/509, 512, 63, 68.1; 366/127, 348; 222/1
See application file for complete search history.

(56) References Cited

U.S. PATENT DOCUMENTS

| | | | | |
|---|---|---|---|---|
| 5,472,603 | A | 12/1995 | Schembri | |
| 5,674,742 | A * | 10/1997 | Northrup et al. | 435/286.5 |
| 6,010,316 | A | 1/2000 | Haller et al. | |
| 6,210,128 | B1 | 4/2001 | Rife et al. | |
| 6,394,759 | B1 | 5/2002 | Parce | |

(Continued)

FOREIGN PATENT DOCUMENTS

DE 100 55 318 12/2001

(Continued)

OTHER PUBLICATIONS

Nature Biotechnology vol. 17, Nov. 1999, pp. 1109-1111.

(Continued)

*Primary Examiner* — Maureen Wallenhorst
(74) *Attorney, Agent, or Firm* — Kilpatrick Townsend & Stockton LLP

(57) ABSTRACT

A method or device for integrated dosing and intermixing of small amounts of liquid, has at least one dosing reservoir (3) connected to a reaction reservoir (1) via at least one joining structure (11) and entirely filled with a first liquid. The at least one joining structure (11) is preferably dimensioned such that surface tension of the first liquid prevents the first liquid from penetrating into the reaction reservoir (1) which is entirely filled with a second liquid contacting the first liquid on the joining structure (11). A flow pattern is created in or on the reaction reservoir (1) to thoroughly mix the two liquids.

24 Claims, 6 Drawing Sheets

U.S. PATENT DOCUMENTS

| | | | |
|---|---|---|---|
| 6,408,878 | B2 | 6/2002 | Unger et al. |
| 6,568,052 | B1 | 5/2003 | Rife et al. |
| 6,777,245 | B2 * | 8/2004 | Wixforth ...................... 436/180 |
| 2001/0055529 | A1 | 12/2001 | Wixforth |
| 2002/0036018 | A1 | 3/2002 | McNeely et al. |
| 2002/0137196 | A1 | 9/2002 | Miles et al. |
| 2003/0000835 | A1 | 1/2003 | Witt et al. |
| 2004/0072366 | A1 | 4/2004 | Wixforth et al. |
| 2004/0091399 | A1 * | 5/2004 | Chung et al. .................. 422/100 |
| 2004/0109793 | A1 | 6/2004 | McNeely et al. |
| 2004/0257906 | A1 * | 12/2004 | Scriba et al. .................. 366/127 |
| 2006/0275883 | A1 * | 12/2006 | Rathgeber et al. ......... 435/173.1 |
| 2008/0186799 | A1 * | 8/2008 | Gauer ........................... 366/127 |

FOREIGN PATENT DOCUMENTS

| | | | |
|---|---|---|---|
| DE | 101 36 008 | | 2/2003 |
| DE | 101 42 789 | | 5/2003 |
| DE | 103 25 307 | | 7/2004 |
| DE | 103 25 313 | | 7/2004 |
| EP | 1418003 | | 5/2004 |
| JP | 2003-535349 | T | 11/2003 |
| JP | 2004-163104 | A | 6/2004 |
| JP | 2004-517335 | T | 6/2004 |
| WO | 03/012389 | | 2/2003 |
| WO | 03/018181 | | 3/2003 |
| WO | 2003/018181 | * | 3/2003 |

OTHER PUBLICATIONS

Science vol. 282, Oct. 16, 1998, pp. 484-486.

Applied Physics Letters, vol. 77, No. 11, Sep. 11, 2000, pp. 1725-1726.

Acoustic Streaming, pp. 265-271.

* cited by examiner

METHOD AND DEVICE FOR DOSING AND MIXING SMALL AMOUNTS OF LIQUID

BACKGROUND OF THE INVENTION

The invention relates to a method for the metering and mixing of small quantities of liquid, to a device and to an apparatus for carrying out the method and to a use.

Diagnostic assays, in particular in the field of clinical chemistry and immunochemistry, are carried out in an automated manner to a large extent today. Defined volumes of sample liquid and reagents are pipetted into a cuvette or into the well of a microtiter plate and mixed in the corresponding automatic units. Subsequently, a first reference measurement is made in which, for example, the optical transmission through the cuvette is determined. After a certain reaction time between the sample and the reagents, a second measurement of the same parameter is made. The concentration of the sample with respect to a specific constituent or also only the presence of the constituent results by the comparison of the measured values. Typical volumes lie in sum at some hundred microliters, with necessary mixture ratios of sample to reagent being able to occur between 1:100 and 100:1. Optionally, a plurality of reagents can also be provided for mixing with a sample. In addition to the instruments just described for a high throughput, which are typically to be found in special laboratories, there are also endeavors to carry out assays in a decentral manner and without any large instrumental effort. It would be desirable in this connection if the "lab-on-a-chip" technology recently introduced could be used in which the processing of liquids on or in a chip be can carried out in an integrated manner. Assay times of less than one hour are desirable.

Microfluid systems are used, for example, for the movement of the liquids in which liquid is moved through electroosmotic potentials, see for example Anne Y. Fu, et al. "A micro fabricated fluorescence-activated cell sorter", Nature Biotechnology Vol. 17, November 1999, p. 1109 ff.

A method for liquid mixing in the microliter range is described in DE 103 25 307 B3 in which small liquid volumes are mixed in microtiter plates with the help of noise-induced flow. Another method for the generation of movement in small quantities of liquid on a solid surface is described in DE 101 42 789 C1. Here, a liquid is mixed or a plurality of liquids are mixed with one another with the help of surface sound waves.

In accordance with a method described in DE 100 55 318 A1, a quantity of liquid is placed onto a region of a substantially planar surface whose wetting properties differ from the surrounding surface such that the liquid preferably remains there, with it being held together by its surface tension. Movement of the quantity of liquid can be generated in this connection by the pulse transfer of a surface sound wave to the liquid.

In particular the integration of the metering and the mixing of the sample and the reagents in a cost-favorable lap-on-a-chip system is problematic. A homogeneous mixing of different quantities of liquid which are so small is difficult to realize.

It is necessary to define volumes of quantities of liquid precisely for the metering. This can be carried out geometrically, for example. For example, in an open system, the wetting properties of the surface can thus determine a volume, as is described in DE 100 55 318 A1. Here, the definition of the volumes takes place by hydrophilic and hydrophobic regions over the wetting angle on a substantially smooth surface. If a plurality of volumes were defined in this manner which should be brought to reaction, the volumes are moved toward one another to achieve this. On the movement on a surface, liquid residues or molecules of the analyte or of the reagent located in the liquid can remain stuck to the surface so that a volume loss or a reduction in concentration of unknown amount cannot be precluded by the movement. In addition, measures must be taken against evaporation which can in particular be problematic with longer assay times.

Other preparations use passages of defined cross-section which are filled with liquid in a capillary manner. If the liquid is an aqueous solution, a hydrophobic barrier which cannot be filled in a capillary manner is attached to the end of the passage. Furthermore, there is a lateral branch at this passage with a likewise hydrophobic surface which cannot be filled in a capillary manner. The cross-section and length of the passage between the hydrophobic barrier and the hydrophobic branch now determine a volume which can be separated and moved in a defined manner by pneumatic pressure through the branch (Burns et al., An integrated nanoliter DNA analysis device, Science 282, 484 (1998)). High costs arise by this type of volume definition due to the necessary wetting structuring of the surface (hydrophilic for the filling of the passage itself and hydrophobic for the barrier and the branch). In addition, it is necessary to work with air pressure, which requires corresponding devices. The passage cross-section must be small to permit the capillary filling of the measurement passage. Long passages are therefore necessary with large volumes in the range of some 100 microliters. This necessarily results in large unwanted interactions of the molecules in the liquid with the passage wall. An efficient mixing of a plurality of quantities of liquid is almost impossible in this geometry.

The term "liquid" in the present text includes inter alia pure liquids, mixtures, dispersions and suspensions as well as liquids in which solid particles are located, for example biological material. Liquids to be metered and to be mixed can also, for example, be two or more similar solutions which only differ by constituents dissolved therein which should be brought to reaction.

SUMMARY OF THE INVENTION

It is the object of the present invention to provide a method and a device with whose help a precise metering of quantities of liquid can be carried out simply in a large dynamic range and which permit a complete mixing of the liquids. The method should be able to be carried out in a compact lab-on-chip system.

This object is satisfied by a method, a device or an apparatus having the features herein. Preferred embodiments and advantageous use are also described herein.

In the method in accordance with the invention for the integrated metering and mixing, a metering reservoir is completely filled with a first liquid and is in communication with a reaction reservoir via at least one connection structure, with the connection structure preferably being dimensioned in relationship to the reservoir such that the surface tension of the first liquid prevents an entry into the reaction reservoir. The cross-section of the connection structure can in particular be selected to be smaller than the cross-section of the reaction reservoir for this purpose. The reaction reservoir is completely filled with a second liquid so that the second liquid comes into communication with the first liquid at the connection structure. Finally, a flow pattern is generated in the liquid in or on the reaction reservoir which results in the mixing of the liquids, with the flow pattern being maintained up to the complete homogenization of the liquids. A laminar flow pattern is preferably generated.

The laminar flow pattern can be generated directly in the reaction reservoir. It is equally possible for the laminar flow to be generated in at least one connection structure in the direction of the reaction reservoir and to act in the reaction reservoir in this manner. Finally, with a corresponding geometrical configuration, is also possible to excite the laminar flow in the metering reservoir such that it acts in the reaction reservoir via the connection structure.

In the method in accordance with the invention, the quantity of the first liquid to be metered in the metering reservoir is fixed. The first liquid is prevented from entering into the reaction reservoir. In a preferred process management, the surface tension prevents the liquid from entering into the reaction reservoir. A liquid exchange can only take place when the first liquid comes into contact with the second liquid which was brought into or onto the reaction reservoir. In this connection, a liquid exchange due to diffusion is negligible due to the smaller cross-section of the connection passage structure. An effective mixing is only effected by generation of a corresponding flow pattern in the reaction reservoir. The quantity of the second liquid is determined by the size of the reaction reservoir.

A metering and mixing of liquids in a large dynamic region, that is with very different mixing ratios can be carried out precisely with the method in accordance with the invention. The mixing ratio between reagents and sample liquid can be set, for example, between 1:100 up to 100:1.

The flow pattern can be generated by radiation of sound waves into the liquid on or in the second reservoir or in the direction of the second reservoir.

Surface sound waves can be used for the generation of sound waves and can be generated in a manner known per se with the help of an interdigital transducer on a piezoelectric chip which is attached to the device. The impulse transfer of the surface sound waves is used either directly or with the help of the sound waves generated with the help of the surface sound wave. The term surface sound waves in the present text also includes interface sound waves at the interfaces between two solid bodies.

The reservoirs and the connection structures can be configured as three-dimensional or as two-dimensional. The reservoirs and connection structures can thus be correspondingly shaped wells in a surface. In different configurations, they are correspondingly shaped hollow spaces. In a two-dimensional configuration, the reservoirs and connection structures are formed by correspondingly shaped regions of a surface which are more preferably wetted by the liquids than the surrounding regions of the surface. Surfaces which are hydrophilic in comparison with their surrounding are selected for the reservoirs and connection structures for aqueous solutions. Such wet-modulated surfaces are described, for example, in DE 100 55 318 A1. The liquids are held together as drops on the preferably wetted regions by their surface tension.

For simpler illustration, if it is not otherwise explicitly set forth, three-dimensional and two-dimensional realizations are each covered in the present text, even if terms are selected which only seem to describe one option. For example, the term “introduction into a reservoir” or “filling” is thus also used for the application of a liquid to a two-dimensional reservoir area. In a similar manner, the term “movement through the connection structure” is, for example, also used, etc., for the movement of liquid on a two-dimensional connection structure. The “volume” or the size of a “cross-section” in an analog manner means the surface or the width, for example, in two-dimensional realizations.

The connection structure can be a correspondingly dimensioned opening between the metering reservoir and the reaction reservoir. A particularly precise process management utilizes the capillary force in a connection capillary structure which is wetted by the first liquid and is filled by the capillary forces from the metering reservoir. The capillary forces decrease abruptly at the inlet point of the connection capillary structure into the reaction reservoir due to the enlarged cross-section so that a discharge of the first liquid from the connection capillary structure into the reaction reservoir is prevented. Only when the second liquid is introduced into the reaction reservoir or is applied onto the reaction surface does the second liquid come into communication with the first liquid so that a mixing can occur.

With a three-dimensional metering device, the reservoirs are filled in an aspect of the metering method through filling openings which are preferably located in the upper termination of the reservoir.

The metering reservoir can be formed by a correspondingly dimensioned volume. In a particularly preferred aspect of the method in accordance with the invention, a reservoir capillary structure is used as the metering reservoir and has at least two openings along its extent. The capillary structure can be filled through an opening. Liquid enters through the first opening and moves up to the second opening driven by the capillary force. The reservoir capillary structure is selected as the capillary structure such that the liquid front of the moving liquid takes up the whole cross-section of the capillary structure. No further openings in the system are open except for the filling opening and the second opening. The liquid stops its movement at the second opening. Since no further venting openings are provided, a counter pressure builds up at the other side of the second opening which prevents a further liquid movement. In addition, the capillary force reduces abruptly at the second opening. A further filling beyond the second opening is therefore not possible up to a specific threshold of the filling pressure. In this manner, a precise volume is defined in the reservoir capillary structure due to the path between the two openings in order to permit a precise metering. In a modification, two second openings arranged symmetrical to the filling opening are used. The liquid volume of the liquid metered in such a reservoir capillary structure then corresponds to the spacing of these two second openings.

A further development uses a reservoir capillary structure having a plurality of such selectable openings which are opened in dependence on the desired metering volume of the first liquid. If openings are opened which are further away from the opening used as the filling opening, the liquid can enter up to these openings and take up a larger volume.

The metering reservoir in this process management corresponds to the volume of the reservoir capillary structure filled with first liquid. The remaining part of the reservoir capillary structure is part of the reaction reservoir.

Open filling structures which are connected to the metering reservoir or to the reaction reservoir via feeds can be used for the filling of the metering reservoir. The respective liquid can be introduced manually or automatically into the respective filling structure with the help of a pipette, for example. The liquid moves into the respective reservoir through the respective feed. In configurations in which the reservoirs are provided as wells or hollow spaces in a solid body, the filling structures are also selected correspondingly. The feeds can then be correspondingly dimensioned passages, for example.

In a further development, the feed or feeds are selected as a capillary structure. The liquid to be introduced then automatically moves out of the filling structure into the respective reservoir due to the capillary forces.

Another advantageous aspect of the method in accordance with the invention uses a plurality of preferably differently sized metering reservoirs which are in communication with the reaction reservoir via connection structures. In addition, the metering reservoirs are in communication with a filling opening. The connection structures between the individual metering reservoirs and the reaction reservoir can first be closed in one configuration and be opened for the selection of the desired metering reservoir. In another aspect, the desired metering reservoir with the desired volume is selected in that the remaining connection structures to the other metering reservoirs are closed.

In a modification of this process management, first all the metering reservoirs are filled and then the connection structure of the desired metering reservoir is opened. In this connection, individual metering reservoirs are optionally filled through other metering reservoirs. Such a process management also makes possible the filling of a larger number of metering reservoirs through only one filling opening and thus only one position of a filling device, e.g. of a pipette tip. This process management has the advantage that the corresponding filling device does not have to be moved and so the device effort is low. Only after the complete opening of all metering reservoirs is the selected metering reservoir connected to the reaction reservoir by opening the corresponding connection structure.

Both the opening and the closing can be effected by a melting process on a suitable selection of the material of the metering device used. A plastic part is, for example, suitable as a metering device. The connection structures are either first closed, with the desired connection structures being melted open prior to use to establish a connection. In another process management, metering device are used in which the connection structures are first open and the connection structures not required are closed by a melting process prior to use.

In another process management, specifically for a two-dimensional configuration, the connection between the two liquids is established via a small "bridging drop" which is brought between the two liquids and generates a liquid bridge. The bridging drop has a smaller volume than both the first quantity of liquid and the second quantity of liquid.

A configuration is particularly advantageous in which more than one connection structure is present between a metering reservoir and the reaction reservoir. The liquid exchange can take place here—driven by sound waves, for example—in a circuit until a complete homogenization of the liquids has occurred.

The method in accordance with the invention is not limited to the metering of one quantity of liquid to a second quantity of liquid. A plurality of quantities of liquid can be provided simultaneously or successively to the metering to the liquid in the reaction reservoir with a corresponding number of metering reservoirs and connection structures which connect these metering reservoirs to the reaction reservoir.

A device in accordance with the invention with which the method in accordance with the invention can be carried out has at least one metering reservoir for a first quantity of liquid. Furthermore, a reaction reservoir for a second quantity of liquid and at least one connection structure between the two reservoirs are provided. The connection structure is preferably dimensioned in relationship with the reservoir such that the first liquid cannot enter into the reaction reservoir due to its surface tension. Finally, the device in accordance with the invention has a device for the generation of preferably one laminar flow pattern for the mixing of liquid in the reaction reservoir.

A preferred embodiment has at least one sound wave generation device for the radiation of sound waves into the reaction reservoir or in the direction of the reaction reservoir for the generation of the flow pattern. The at least one sound wave generation device is preferably formed by a surface sound wave generation device, in particular by an interdigital transducer on a piezoelectric chip.

The reservoirs and the at least one connection structure can be configured as wells or as hollow spaces in a solid body. In a two-dimensional configuration of the device in accordance with the invention, the reservoirs and connection structures are formed by correspondingly shaped regions of a surface which are more preferably wetted by the liquids than the surrounding regions of the surface. Such wet-modulated surfaces are described, for example, in DE 100 55 318 A1.

A three-dimensional embodiment of the metering device in accordance with the invention can, for example, include wells in a solid body which are closed by a cover to form the reservoirs or connection structure. The cover can be made in a simple manner from a foil, preferably of plastic.

An apparatus in accordance with the invention with which the method in accordance with the invention can be carried out while using a device in accordance with the invention includes a receiver for a device in accordance with the invention. When the device is inserted, the at least one device for the generation of a flow pattern is electrically contacted. The apparatus in accordance with the invention furthermore has controllable filling devices. e.g. pipettes or dispensers, which are arranged above the filling structures when the device is introduced into the receiver. The precision demands on the filling devices are not very high when using a device in accordance with the invention or when carrying out the method in accordance with the invention since the metering only takes place inside the device itself. Finally, the apparatus has a control for the control of the time procedure of a protocol which takes over the control of the device for the generation of the flow pattern and of the filling devices. Preferred embodiments include opening devices for the opening of individual filling structures, venting openings or barrier structures or devices for the closing of individual barrier structures.

The device in accordance with the invention can also satisfy other functions with a corresponding equipping, e.g. if a heating device is provided for the temperature control. Finally, the e.g. electrical or optical evaluation an also be integrated as well.

The method in accordance with the invention can be carried out simply and in an automated manner using an apparatus in accordance with the invention. Disposable parts can be used without problem as devices in accordance with the invention for the integrated metering and mixing.

Advantages of the device in accordance with the invention, of the apparatus in accordance with the invention and preferred embodiments of the dependent claims result from the above description of the advantages and preferred configurations of the method in accordance with the invention.

The method in accordance with the invention, the device in accordance with the invention and the apparatus in accordance with the invention can be used particularly effectively for the metering and mixing of biological liquids in which a precise metering of very small quantities of liquid is required.

BRIEF DESCRIPTION OF THE DRAWINGS

Embodiments and aspects of the invention will be explained in detail with reference to the enclosed Figures. The Figures are not necessarily to scale and serve for schematic presentation. There are shown.

DESCRIPTION OF THE PREFERRED EMBODIMENTS

Figure 1:
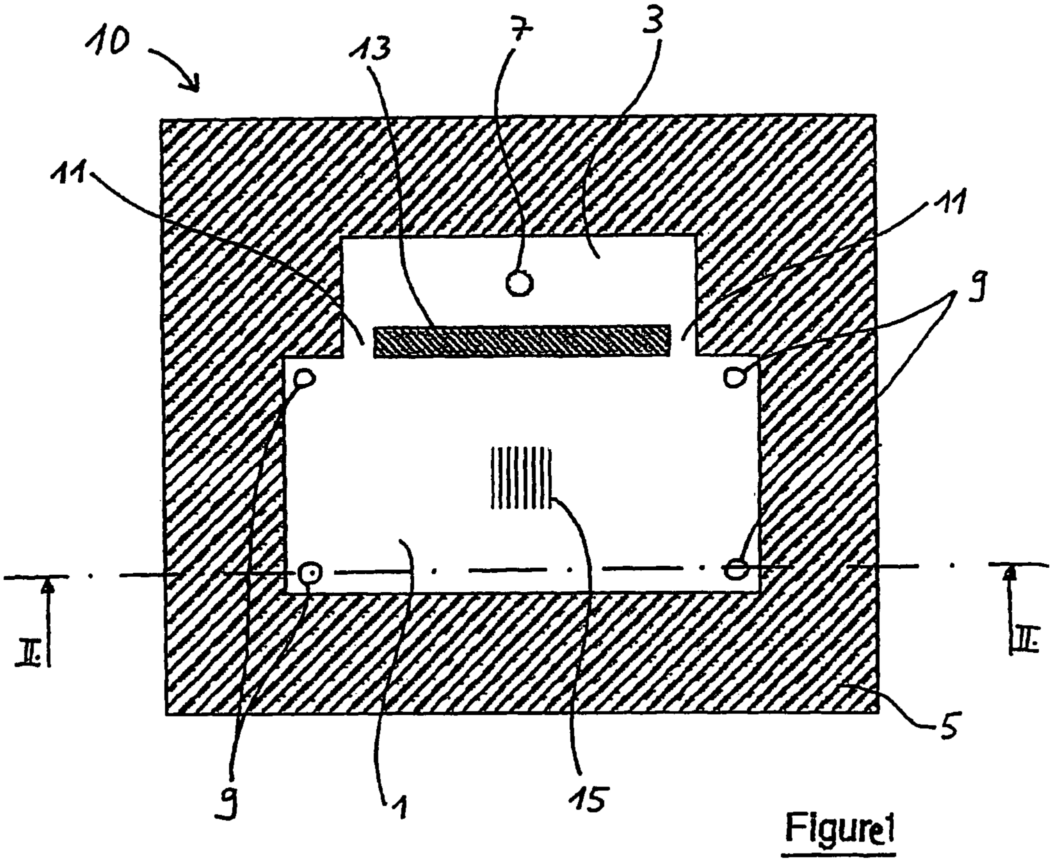
FIG. 1 a plan view of a metering device in accordance with the invention in an open state.

FIG. 1 shows a plastic part with chambers 1, 3. The plastic part 5 can, for example, be manufactured in an injection molding process. The cover of the chamber is effected by a thin plastic foil 2 which is laminated on and which is visible in FIG. 2 and is not shown in FIG. 1 to illustrate the inner workings of the plastic part 5. The connection between the chambers 1 and 3 takes place via two restrictions 11. Reference numeral 13 designates the wall between the chambers 1 and 3.

In FIG. 1, the positions of the filling openings 7 and 9 are indicated which are provided in the plastic foil 2 which is, however, not shown in FIG. 1.

An acoustic chip 15 is located beneath the chamber 1, which also called a reaction chamber in the following, said chip for example being able to be a piezoelectric solid body chip on which an interdigital transducer is applied in a manner known per se for the generation of surface sound waves. The interdigital transducer is configured such that the surface sound waves generated with it permit a sound wave radiation into the reaction chamber 1. The radiation of sound waves into a liquid volume which is separated from the interdigital transducer generating surface sound waves by a solid body is described in DE 103 25 307 B3. In an analog manner, the acoustic chip 15 can also be provided on the foil 2 or in a side region.

The acoustic chip 15 is connected via electrical connections, not shown, to an alternating voltage source with which an alternating voltage of a frequency of some 10 MHz can be generated in order to generate surface sound waves with the interdigital transducer which result in the radiation of sound waves into the reaction chamber 1.

The position of the acoustic chip 15 is indicated in FIG. 1, although the chip would not be visible per se in this view since it is attached to the lower side of the device in the embodiment shown. In the sketch of FIG. 1, the acoustic chip is drawn in the form of parallel lines which should only schematically indicate the alignment of the individual finger electrodes of the interdigital transducer on the piezoelectric chip 15. The radiation direction of the surface sound waves of an interdigital transducer aligned in this manner is perpendicular to the alignment of the finger electrodes.

The required size of the chamber 1 serving as the reaction reservoir depends on the frequency of the sound waves used. In this connection, the smallest extent should be very much larger than the wavelength of the sound used. Finally, the extent of the reaction chamber 1 in the propagation direction of the sound waves should be approximately one order of magnitude larger than the extent of the restrictions 11. The smallest extent of the reservoir amounts, for example to 1 mm to 10 mm at a sound wavelength of, for example, 100 μm. The total length of the passage system amounts to some centimeters. The filling openings 7, 9 are at least one order of magnitude smaller than the reaction chamber 1.

The device in accordance with the invention of this embodiment is used as follows. The reaction reservoir comprises, for example, 100 μl or 150 μl whereas the metering reservoir comprises 5 μl. Such liquid volumes are in particular characteristic for a number of diagnostic applications. First, the metering reservoir 3 is filled with a first liquid through the filling hole 7, which can take place through capillary force, for example. The liquid will stop at the restrictions 11 since here the capillary force becomes abruptly smaller due to the large diameter of the reservoir 1. Subsequently, the reservoir 1 is filled with a second liquid through the filling holes 9. A possible overspill of liquid on the respective filling holes 7, 9 is not critical. The liquid of this overspill does not participate in the following mixing process for geometrical reasons, in particular when the following mixing process is effected by a laminar flow pattern. In this manner, the volumes of the two liquids are now geometrically defined without any great precision of the filling devices used, pipettes for example, being necessary. The liquids are in contact at the restrictions 11. Diffusion only takes place to a negligible extent due to the narrow cross-section of the restrictions 11. A homogenous mixing of the total quantities of liquid is achieved with the help of the acoustic chip 15. Acoustic energy is radiated into the defined volumes of the liquids by application of an alternating voltage to an acoustic chip and a lamina flow pattern is generated. The liquids or their constituents are mixed and optionally brought to reaction. The result of this reaction can be read off optically or electrically, for example. It is of advantage in this connection that the filling holes 7, 9 do not have to be closed.

The metering and mixing of the liquids therefore takes place in a cost-favorable device 5 optionally configured as a disposable cartridge. The metering is additionally very simple. Even if an overspill of the filling holes occurs, it will not participate in the mixing reaction for geometrical reasons and/or due to the laminar flow pattern used.

Figure 2:
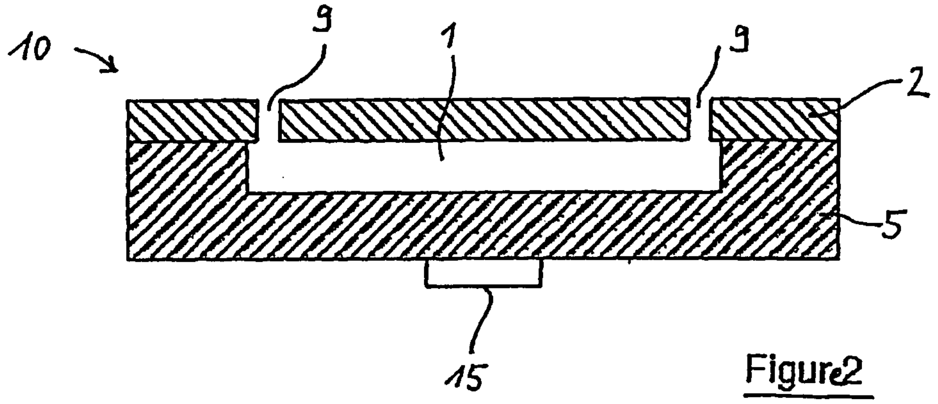
FIG. 2 a cross-section in the direction of view II through the embodiment of FIG. 1.
Figure 3:
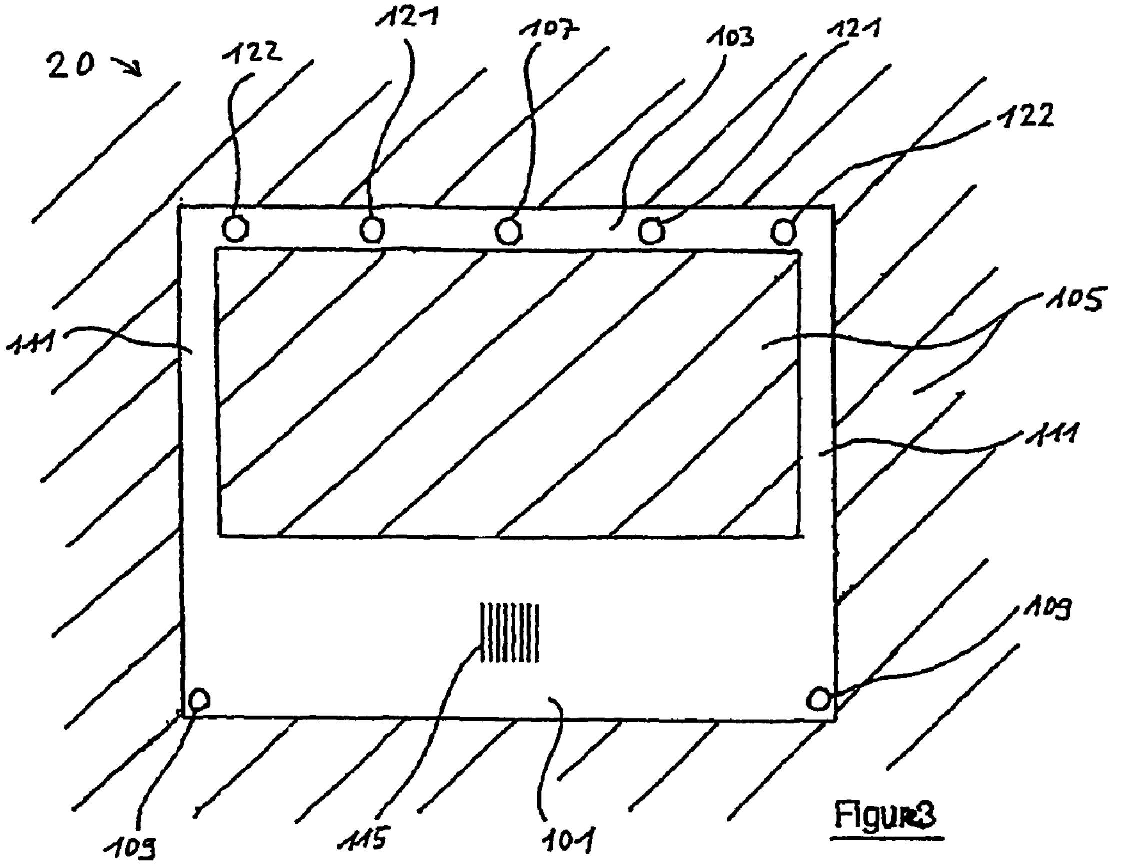
FIG. 3 a plan view of a further embodiment of a metering device in accordance with the invention.

FIG. 3 shows another embodiment of a metering device in accordance with the invention. What is shown here is the portion of a plastic body 105 which contains the metering device which likewise includes the wells in the plastic structure 105. The reaction reservoir 101 with filling holes 109 is visible. 103 shows a capillary structure having a plurality of openings, with the opening 107 serving as the filling opening. The capillary structure 103 represents a metering capillary structure which is in communication with the reaction reservoir 101 via connection capillary structures 111. The total structure is likewise closed by a plastic foil. The openings 107, 109, 121 and 122 not visible per se in the open representation are also indicated in this embodiment to show their relative position. The acoustic chip 115 with an interdigital transducer is likewise indicated in its position arranged beneath the device and accordingly not actually visible in the illustration. The acoustic chip 115 corresponds to the chip 15 described with reference to FIGS. 1 and 2.

Different mixing ratios can be set using such a metering device. The filling takes place via the filling hole 107 which is open. All other holes 109, 121, 122 are first closed. The volume of the first liquid filled in can now be set by selective opening of the holes 121, 122. If e.g. only one hole 121 in direct proximity to the filling opening 107 and the hole 121 arranged symmetrically thereto on the other side are open, a liquid volume can be defined of a length which corresponds to the spacing between the two open openings 121.

The capillary structure 103 in this connection has the effect that the front of the liquid fills up the total cross-section of the capillary structure 103. If no further venting holes are open, a counter-pressure is built up which results in the stopping of the liquid. A movement beyond the opened holes 121 is therefore not possible. This effect is amplified in that the capillary force effecting the movement becomes smaller through the open opening 121.

If the two outer openings 122 are opened, a correspondingly larger volume results.

In both cases, the residual volume in the passage 103 and the connection capillary structures 111 can be filled via the reaction reservoir 101 through the openings 109 then to be opened. The residual volume of the passage 103 then counts toward the reaction reservoir.

The characteristic dimensions of an embodiment in accordance with FIG. 3 correspond to the characteristic dimensions of FIGS. 1 and 2.

With such an embodiment, the setting of different mixing ratios is therefore possible in a simple manner. Depending on how much of the first liquid should be metered to the second liquid, the corresponding openings 121, 122 are opened. This can take place, for example, by a simple piercing of the plastic foil at correspondingly marked positions. The further function substantially corresponds to the embodiment of FIGS. 1 and 2.

Figure 4:
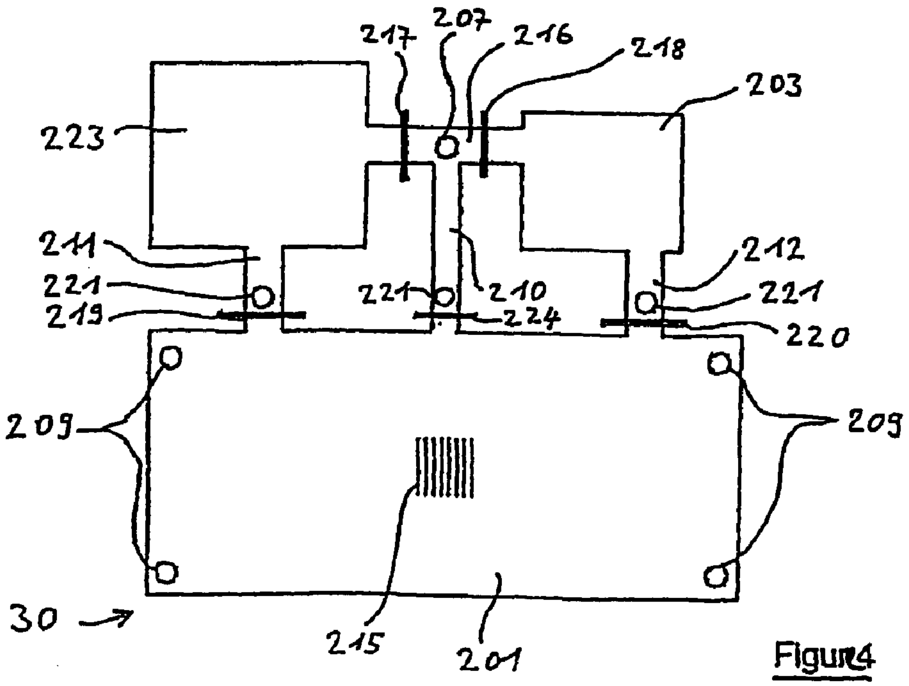
FIG. 4 a plan view of a third embodiment of the metering device in accordance with the invention, FIG. 5 a plan view of a fourth embodiment of the metering device in accordance with the invention.

FIG. 4 shows another embodiment. A plurality of metering reservoirs 203, 223 are provided here which are in communication with the reaction reservoir 201 via connection capillary structures 211, 212. The metering reservoirs 203, 223 have differently sized volumes and are in communication via a connection passage structure 216. The filling opening 207 is located in the connection passage structure 216. The metering reservoirs 203, 223 have venting openings 221. The connection passage 216 in the embodiment shown is likewise connected to the reaction reservoir 201 via a connection capillary structure 210. The structure 210 also comprises a venting hole 221. Finally, filling openings 209 are provided in the reaction reservoir 201.

217, 218, 219, 220 and 224 schematically represent barrier structures. The total metering device of FIG. 4 is provided in a plastic part which is terminated by a film having openings 207, 209, 221. The metering device of FIG. 4 can likewise be a disposable part which is prefabricated ex works. In this connection, the barrier structures 217, 218, 219, 220, 224 are first made closed in the embodiment shown.

The filling openings 207, 209 and the venting openings 221 which are not visible per se in the open position are also indicated in their position in the illustration of FIG. 4. In addition, an acoustic chip 215, which corresponds to the already described acoustic chip 15, 115 is located beneath the arrangement of FIG. 4. The acoustic chip 215 is also indicated in FIG. 4, although it is not visible per se in this illustration since it is located beneath the arrangement.

The characteristic dimensions in the embodiment of FIG. 4 also correspond to the characteristic dimensions of the embodiment of FIGS. 1 and 2.

A decision is first made for the use of the embodiment in a process management as to which of the metering reservoirs 203, 223 should be filled with liquid to define a corresponding volume of liquid. The metering reservoir 223 is selected for explanation in the present description. After the selection has been made, the corresponding barriers 217, 219 adjoining the metering reservoir 223 are melted open, for example by a heater or using laser energy. This can, for example, take place with the help of an automatic machine which processes the metering device.

The correspondingly selected metering reservoir 223 can then be filled via the filling opening 207 and be used for the metering. In this connection, the metering is carried out in a similar manner, for example, as described in the embodiment of FIGS. 1 and 2. The dimensions of the structures are in particular selected such that a filling of the metering reservoir can take place through the effect of the capillary force. Alternatively, a filling can take place with pressure. The deaeration opening 221 is arranged such that a complete filling of the reservoir is possible.

The liquid does not enter into the reaction reservoir 201 due to the capillary effect which becomes abruptly smaller at the inlet position of the connection capillary structure 211 into the reaction reservoir 201. Only on the filling of the reaction reservoir 201 through the filling openings 209 does liquid from the reaction reservoir 201 come into communication with liquid in the connection capillary structure 211. The further function substantially corresponds to the embodiment of FIGS. 1 and 2.

If the reservoir 203 is selected, the procedure is analogous while using the corresponding barrier structures 218, 220 and the connection capillary structure 212.

Another aspect of this embodiment does not comprise any barrier structures 217, 219 ex works. A decision is in turn first made before use as to which of the metering reservoirs 203, 223 should be used. If e.g. metering reservoir 223 is selected, the other metering reservoir 203 is decoupled with the help of an automatic machine which melts the corresponding connection passage structures closed by application of heating energy or laser energy at the positions of the barriers 218, 220 which are adjacent to the meter reservoir 203 not to be used.

The individual metering reservoirs 203, 223 can also each be connected to the reaction reservoir 201 via a plurality of connection capillary structures 211, 212, which are open on the selection of the corresponding metering reservoir, in the embodiments in accordance with FIG. 4.

In addition to the connection structures 211, 212 with the barrier structures 219, 220, a further connection capillary structure 210 can be provided which connects the connection passage 216 to the reaction reservoir 201. This connection capillary structure 210 also includes a venting opening 221 and, optionally, a barrier structure 224. The additional passage 210 can serve for the forming of a circuit which promotes an effective mixing. After one of the metering reservoirs 203, 223 has been selected, it is filled. Let this again be the metering reservoir 223 for the purpose of the description. An embodiment is first described in which the barrier structures 217, 218, 219, 220, 224 are first closed. The barrier structure 217 is melted open as described for the filling of the reservoir 223. Liquid which fills the metering reservoir 223 and the connection capillary structure 211 is introduced through the filling opening 207. The connection capillary structure 210 is also filled with this liquid. The filling takes place through capillary force, for example.

The barrier structures 219, 224 can now be melted open. The liquid does not enter into the reservoir 201 due to the capillary effect which becomes abruptly lower at the inlet positions of the connection capillary structures 211, 210. The filling of the reservoir 201 with a second liquid through the openings 209 effects the contact of the liquids at the inlet positions of the connection capillary structures 210, 211. The generation of a laminar flow, for example, with the acoustic chip 215 then effects an effective mixing of the liquids. A circuit movement of the liquids can occur in this connection.

With such an embodiment utilizing capillary forces in the connection capillary structures 210, 211, 212, the barrier structures 224 can also be completely dispensed with. Particularly with an embodiment having only two metering reservoirs, as is shown in FIG. 4, the connection capillary structure 210 in every case participates in the circuit process so that a decoupling is not necessary.

In another process management, the barrier structures 219, 224 are only melted open after introduction of the second liquid into the reservoir 201. The process management is otherwise the same. With such a process management, the connection structures 210, 211, 212 do not necessarily have to exert capillary action on the liquids.

Another process management using a device in accordance with FIG. 4 uses barrier structures 217, 218, 219, 220, 224 which are originally open. First liquid is introduced through the filling opening 207. It flows due to capillary effect into the metering reservoirs 203, 223 and into the connection capillary structures 210, 211, 212. They do not enter into the reaction reservoir 201 since the capillary effect breaks down at the inlet positions of the connection structures 210, 211, 212 into the reaction reservoir 201. Only now is a decision made as to which metering reservoir, and thus which metering volume of the first liquid, should be used. Let this again be the metering reservoir 223 for the purpose of the present description. The barrier structures 218, 220 are then melted closed as described and the metering reservoir 203 not used with the liquid located therein is thus decoupled. Then the second liquid is filled into the reaction reservoir 201. The process management following thereon corresponds to the already described circuit process management.

Figure 5:
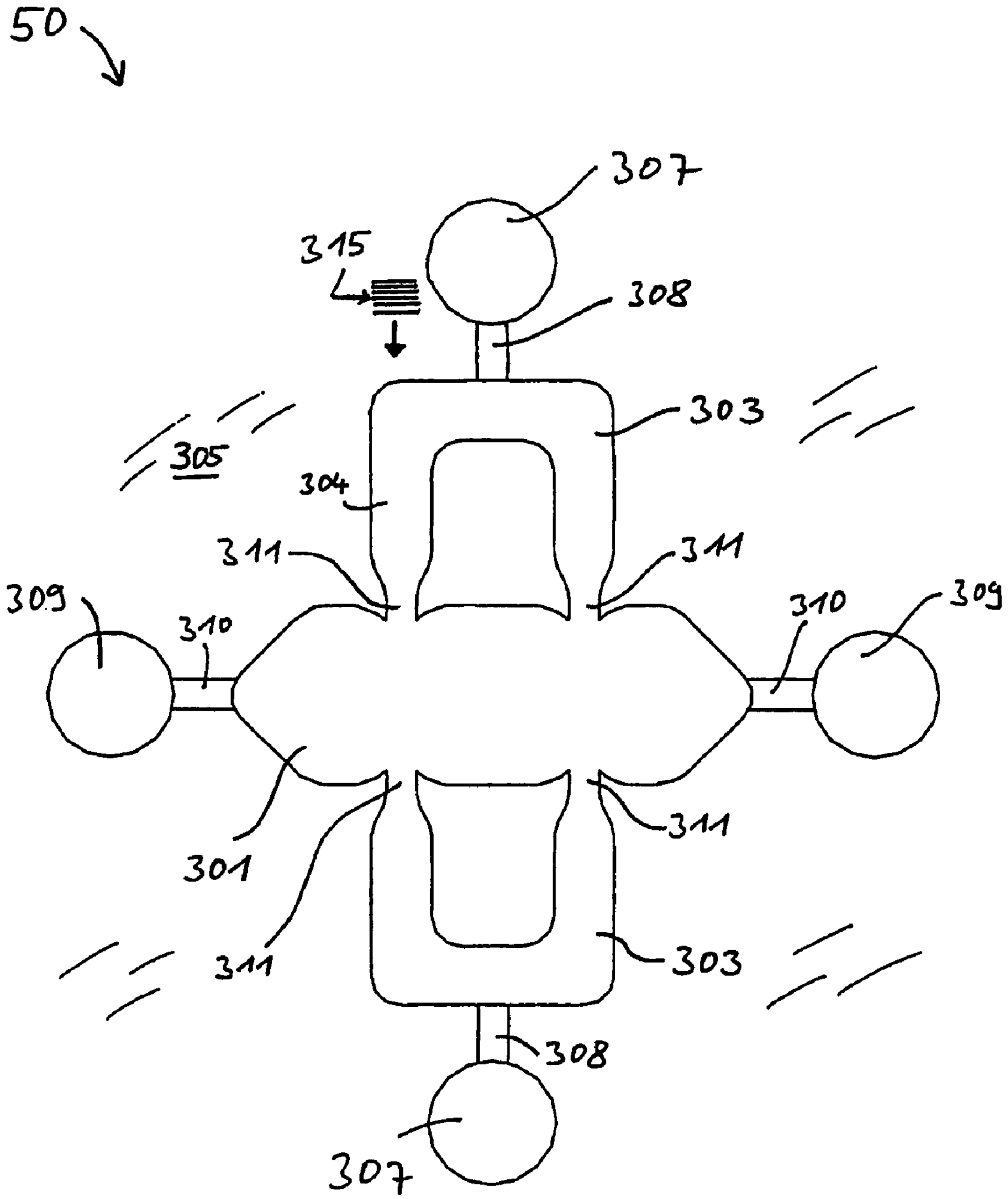

FIG. 5 shows the schematic plan view of a further embodiment of a metering device in accordance with the invention. The total arrangement 50 is arranged at the surface of a plastic carrier 305. The reaction reservoir 1 is formed, for example, by a milled well of a depth of 1 mm and has a volume of, for example, 20 μl. In the example shown, two metering reservoirs 303 adjoin this and are formed, for example, by wells milled with a depth of 1 mm and each having a volume of 10 μl. The metering reservoirs adjoin the reaction reservoir 301 via two respective restrictions 311. Filling structures 307 and 309 are connected to the metering reservoirs 303 or to the reaction reservoir 301 respectively via feeds 308 and 310 respectively. The filling structures 307, 309 are likewise formed, for example, by 1 mm deep wells in the plastic carrier 305. The feeds 308, 310 are wells with a depth of 300 μm in the example shown. A plastic foil, not visible, similar to the plastic foil 2, as can be recognized in FIG. 2, is located over the total arrangement. In the region of the filling structures 307, 309 to be used, this plastic foil is pierced as required, for example, to be able to introduce liquid with the help of a pipette.

315 designates, in a schematic representation, an interdigital transducer which is formed from a large number of mutually engaging finger electrodes. The function was already explained above with respect to the other embodiment. When an electric alternating field is applied to the interdigital transducer, a pulse can be transmitted in the direction of the arrow drawn to the liquid in the limb 304 of the metering reservoir 303 shown in the upper half of the Figure.

FIGS. 6*a* to 6*f* show a sequence in the carrying out of a method in accordance with the invention with the embodiment of FIG. 5. Lines 320 and 322 were drawn to indicate the arrangement of the reaction reservoir 301 with the feeds 310 and the filling structures 309 which would otherwise not be recognizable in the illustrations of FIGS. 6*a* to 6*f* due to the contrast being too low.

In the Figures, in each case only a portion is shown in which one of the metering reservoirs 303 is completely visible.

Figure 6A:
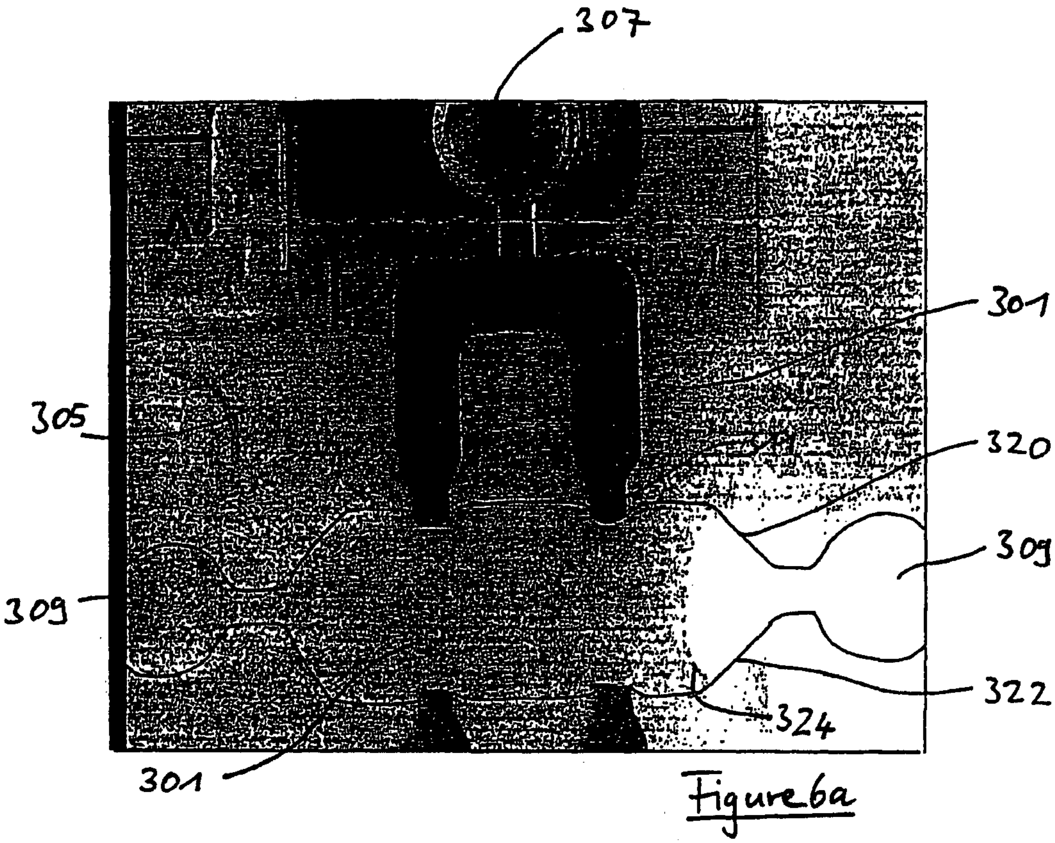
FIGS. 6*a*-6*f* different stages in the carrying out of a method in accordance with the invention having this embodiment.

FIG. 6*a* shows a state in which a liquid, with a dark color here, is filled into the metering reservoir 303 through the filling structure 307 and the feed 308. For this purpose, the covering plastic foil was pierced in the region of the filling structure 307 and the liquid was introduced into the filling structure using a pipette. It can be clearly recognized that the liquid with a dark color does not enter into the still empty reaction reservoir 301 due to its surface tension at the restrictions 311. The volume is precisely defined in the metering reservoir 303 between the restrictions 311 and the feed 308 (in the example shown 10 μl).

A liquid with a light color was thereupon introduced into the reaction reservoir 301. FIG. 6*a* shows the start of this filling process. For this purpose, the covering plastic foil was pierced in the region of the right hand filling structure 309 and it was started to fill in liquid with the help of a pipette. This liquid flows through the feed 310 into the reaction reservoir. It can be recognized in FIG. 6*a* that this process is currently on-going. The liquid border is located approximately at the dotted auxiliary line 324 in this snap-shot.

Figure 6B:
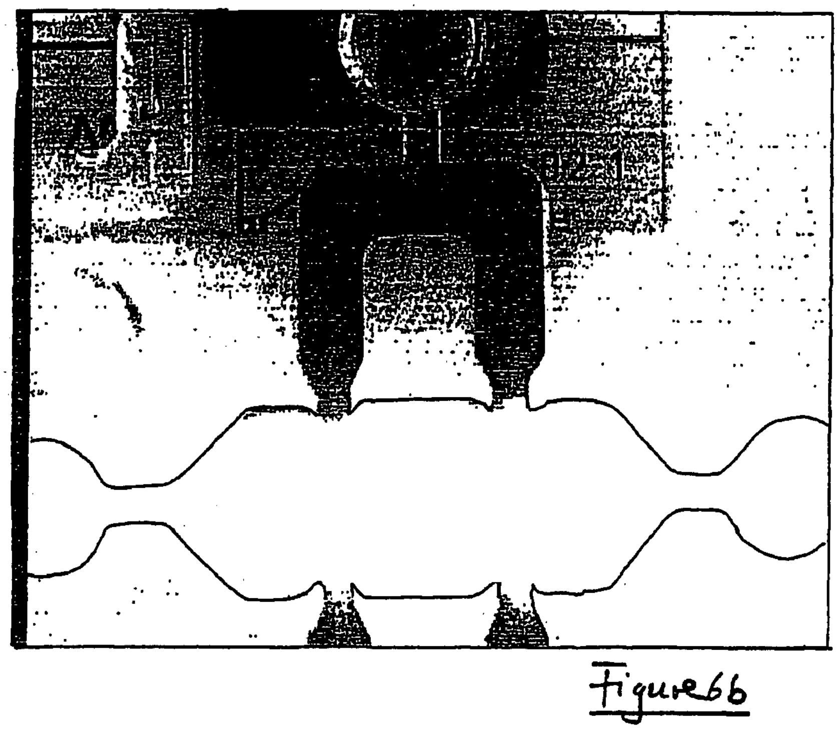

FIG. 6*b* shows a state in which the whole reaction reservoir 301 is filled with the light liquid. A liquid exchange with the dark liquid in the metering reservoir 303 has only taken place to a very limited degree at this point in time.

Figure 6C:
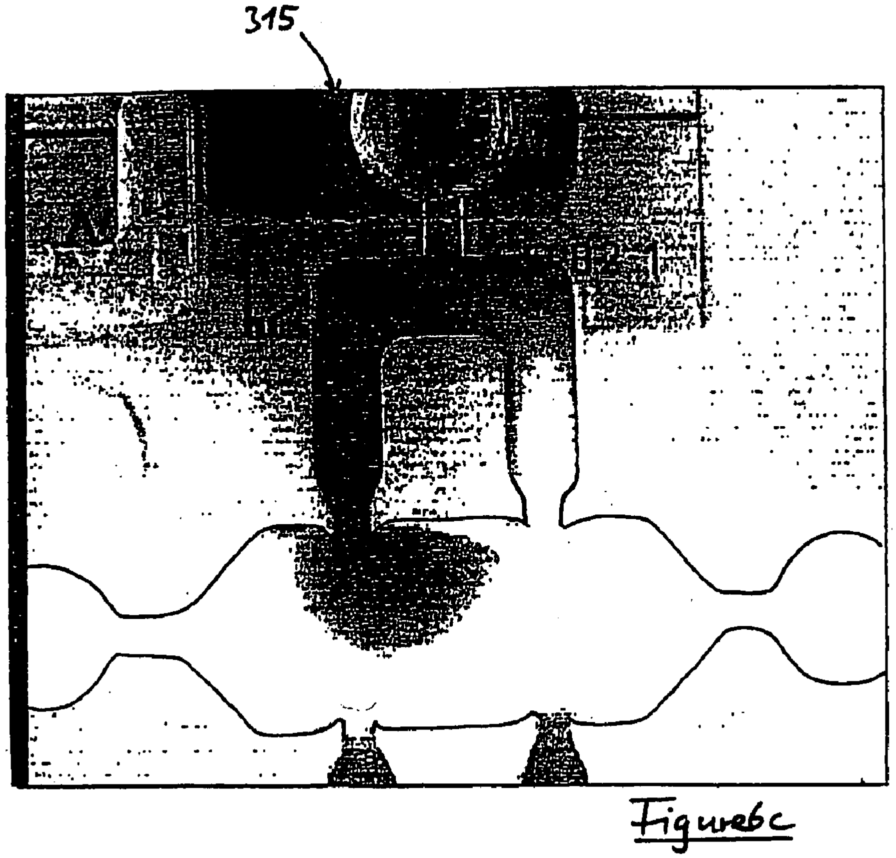
Figure 6D:
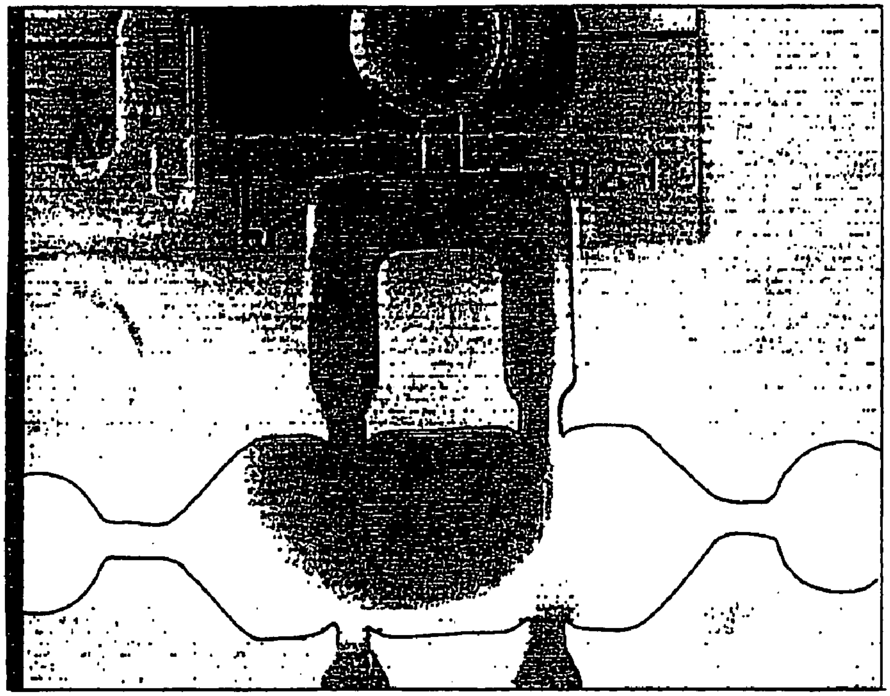
Figure 6E:
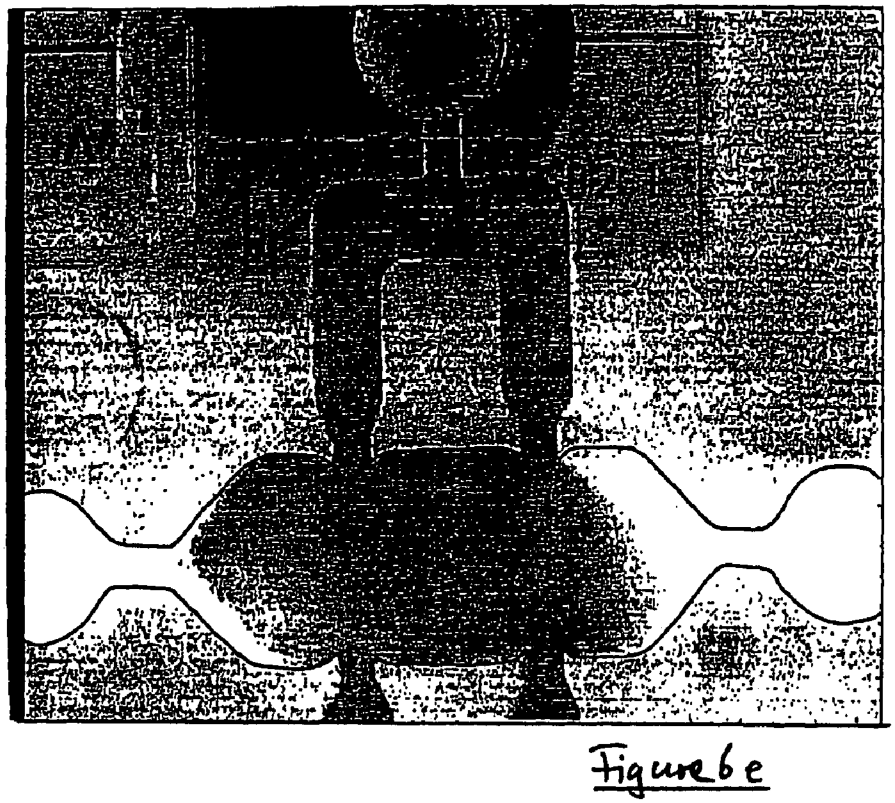

The application of an electrical alternating field to the interdigital transducer 315 effects a pulse transfer to the liquid in the left hand limb 304 of the metering reservoir 303. FIG. 6*c* shows how the laminar flow thereby generated in the metering reservoir 303 has the effect that the dark liquid enters into the reaction reservoir 301. FIGS. 6*d* and 6*e* show the continuation of this process. It can clearly be recognized how the dark liquid, which was originally located in the metering reservoir 303, and the light liquid, which was located in the reaction reservoir 301, mix.

Figure 6F:
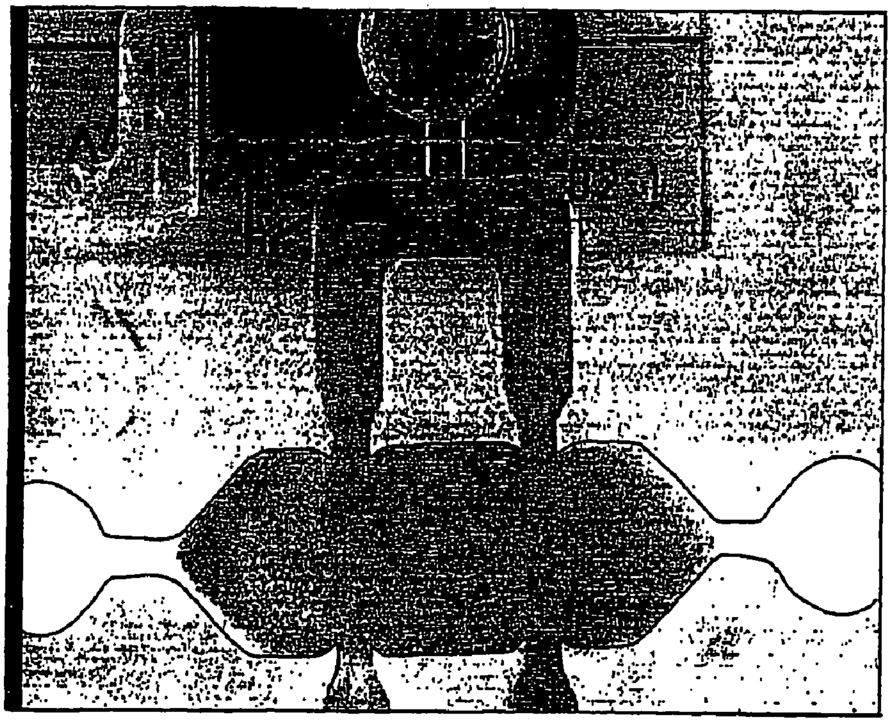

FIG. 6*f* shows the state at the end of the process. The liquids in the metering reservoir 303 and in the reaction reservoir 301 are mixed homogeneously, which can be recognized by the homogeneous shading. A further exchange with the liquid in the feeds 310 from the filling structures 309 to the reaction reservoir 301 has not taken place. The quantity of the supplied light liquid is therefore exactly determined by the dimensions of the reaction reservoir 301. Since the dimensions of the metering reservoir 301 precisely fix the quantity of the metered dark liquid, a very precise metering process has thus been carried out so that the quantities of the different liquids in the mixture present in FIG. 6*f* are precisely determined.

The embodiment shown in FIGS. 5 and 6 has two metering reservoirs 303. Other embodiments only have one metering reservoir or even more metering reservoirs in order to be able to meter different quantities. The two metering reservoirs 303 shown are of equal size in this embodiment. To be able to meter different quantities, differently sized metering reservoirs can also be used.

Barrier structures such as were described with reference to FIG. 4 can also be provided with an embodiment of FIGS. 5 and 6. In this manner, the number of connected metering reservoirs can also be monitored, as is also described for the embodiment of FIG. 4.

In FIG. 5, only an interdigital transducer 315 is shown by way of example. However, even more interdigital transducers can be provided on the plastic carrier 305 to be able to address different metering reservoirs at different points in time and to be able to generate laminar flow in the individual metering reservoirs to effect a mixing with a liquid in the reaction reservoir.

FIGS. 6*a* to 6*f* show that the method in accordance with the invention in particular also results in a laminar flow mixing the liquids without a pressure build-up.

A device in accordance with the invention can also include more than two metering reservoirs with corresponding connection structures. A plurality of metering reservoirs can then be connected "in series" in the circuit to enlarge the metering volume of the first liquid. With such an embodiment, the individual metering reservoirs can have different or equal sizes.

Specifically with a process management in which a circuit of the liquids is used, a reaction between the liquids does not only take place in the part of the device designated by reservoir reaction. For delineation with respect to the use of the term "metering reservoir" with which the metering of the first liquid is carried out, the term "reaction reservoir" was nevertheless used in the present text since, in particular with the embodiment shown, the reaction reservoir is the main structure in which the reaction takes place due to its size. It is, however, also possible in particular with the embodiments in accordance with FIG. 1, FIG. 4 or FIG. 5, for example, that the metering reservoirs and the reaction reservoir are e.g. of equal size and a reaction also takes place in both reservoirs with a circuit process management.

The metering and mixing device in accordance with the invention can be processed in an automatic machine which fills the liquids into the device, temperature controls the device, controls the chips and also opens filling holes or closes or opens barriers. In addition, the electrical or optical evaluation can e.g. optionally also be carried out using such an automatic machine. Such automatic machines can sensibly be used in diagnostics or generally in the automation of the laboratory.

It can therefore be advantageous, for example, if, in the embodiments in accordance with FIG. 3, 4 or 5, the filling of the reservoirs only takes place through one or at most two filling structures since this simplifies the adding of the liquid through the automatic machine. Corresponding pipetting heads or dispensers for filling can then be configured as stationary.

Total volumes of up to 1 ml with individual volumes of e.g. only 100 nl can be processed, for example, with the embodiments shown.

A metering and mixing of liquids in a large dynamic region, that is with very different mixing ratios, can be carried out precisely with the method in accordance with the invention. The demands on the precision of the filling devices used are not high since the metering takes place by the process management in accordance with the invention or by the use of the device in accordance with the invention. The mixing ratio between reagents and sample liquid can be set, for example, between 1:100 up to 100:1.

REFERENCE NUMERAL LIST

1 reaction reservoir, reaction chamber
2 plastic foil
3 metering reservoir, metering chamber
5 plastic part
7, 9 filling openings
10 device for the integrated metering and mixing
11 restrictions
13 boundary wall
15 acoustic chip
20, 30, 50 device for the integrated metering and mixing
101 reaction reservoir, reaction chamber
103 metering capillary structure
105 plastic part
107, 109 filling openings
111 connection capillary structure
115 acoustic chip
121, 122 openings
201 reaction reservoir, reaction chamber
203 metering reservoir, metering chamber
207, 209 filling openings
210, 211, 212 connection capillary structures
215 acoustic chip
216 connection passage structure
217, 218, 219, 220 barrier structures
221, 222 venting openings
223 metering reservoir, metering chamber
224 barrier structure
301 reaction reservoir, reaction chamber
303 metering reservoir, metering chamber
304 part of a metering reservoir
305 plastic part
307, 309 filling structures
308, 310 feeds
311 restrictions
315 interdigital transducer
320, 322 auxiliary lines
324 liquid boundary

The invention claimed is:

1. A method for the integrated metering and mixing of small quantities of liquid, comprising the steps of:

completely filling at least one metering reservoir (3, 103, 203, 223, 303) that is in communication with a reaction reservoir (1, 101, 201, 301) via at least one connection structure (11, 111, 211, 212, 311) with a first liquid, wherein said at least one connection structure is dimensioned such that the surface tension of the first liquid prevents an entry into the reaction reservoir (1, 101, 201, 301);

completely filling said reaction reservoir (1, 101, 201, 301) with a second liquid whereby the second liquid comes into communication with the first liquid at said at least one connection structure (11, 111, 211, 212, 311); and producing a flow pattern at least in or on said reaction reservoir (1, 101, 201, 301) using a sound wave generation device that causes the mixing of the first and second liquids.

2. A method in accordance with claim 1, wherein a substantially laminar flow pattern is generated for the mixing.

3. A method in accordance with claim 2, wherein the laminar flow pattern is generated at least in said at least one connection structure (311) between the metering reservoir (303) and the reaction reservoir (301).

4. A method in accordance with claim 3, wherein sound waves are used for the generation of the laminar flow pattern.

5. A method in accordance with claim 4, wherein the sound waves are generated with surface sound waves with the help of at least one interdigital transducer.

6. A method in accordance with claim 1, wherein sound waves are radiated into the liquid in or on the reaction reservoir (1, 101, 201, 301) for the mixing.

7. A method in accordance with claim 1, wherein the at least one connection structure includes a connection capillary structure.

8. A method in accordance with claim 1, wherein the reservoirs and the at least one connection structure are formed by surface regions on a surface which are preferentially wetted by the liquids in comparison with the surrounding surface.

9. A method in accordance with claim 1, wherein the reservoirs and the at least one connection structure are formed by wells in a surface.

10. A method in accordance with claim 1, wherein the reservoirs (1, 3, 101, 103, 201, 203, 223) and the at least one connection structure (11, 111, 210, 211, 212) are formed by hollow spaces in a solid body structure (5, 105).

11. A method in accordance with claim 10, wherein the reservoirs (1,3, 101, 103, 201, 203, 223) are filled via filling openings (7, 9, 107, 109, 207, 209).

12. A method in accordance with claim 10, wherein a reservoir capillary structure (103) is used as the metering reservoir and has at least two openings (107, 121, 122) along its longitudinal extent.

13. A method in accordance with claim 12, wherein the volume of said first liquid is selected by the selection of the openings (121, 122) in the reservoir capillary structure (103) to be opened.

14. A method in accordance with claim 1, wherein at least one open filling structure (307) is used for the filling of the at least one metering reservoir (303) and is connected to the at least one metering reservoir (303) via feeds (308).

15. A method in accordance with claim 14, wherein at least one capillary structure is used as the feeds (308, 310).

16. A method in accordance with claim 1, wherein at least one open filling structure (309) is used for the filling of the reaction reservoir (301) and is connected to the reaction reservoir (301) via feeds (310).

17. A method in accordance with claim 1, wherein a device having a plurality of metering reservoirs (203, 223, 303) is used, said metering reservoirs being in communication with the reaction reservoir (201, 301) via connection structures (211, 212, 311), on the one hand, and with a filling opening (207, 307), on the other hand.

18. A method in accordance with claim 17, wherein the connection structures (211, 212) are first closed and are opened for the selection of the desired metering reservoir (203, 223).

19. A method in accordance with claim 18, wherein the opening or closing of the connection structures (211) is effected by a melting process in a plastic part.

20. A method in accordance with claim 17, wherein the reservoirs and the at least one connection structure are formed by wells in a surface, and desired metering reservoir (203, 223) is selected by closing the connection structures (211, 212) to the remaining metering reservoirs.

21. A device for the integrated metering and mixing of small quantities of liquid for the carrying out of the method in accordance with claim 1, comprising:

at least one metering reservoir (3, 103, 203, 223, 303) for a first quantity of liquid, wherein the at least one metering reservoir includes a metering capillary structure (103);

a reaction reservoir (1, 101, 201, 301) for a second quantity of liquid;

at least one connection structure (11,111, 211, 212, 311) between the at least one metering reservoir and the reaction reservoir, with the connection structure being dimensioned such that when the metering reservoir is completely filled with the first liquid said first liquid does not enter into the reaction reservoir (1, 101, 201, 301) due to its surface tension, wherein the metering reservoir and the reaction reservoir (1, 3, 101, 103, 201, 203, 223) and the at least one connection structure (11, 111, 210, 211, 212) include hollow spaces in a solid body structure (5, 105); and a device (15, 115, 215, 315) for the generation of a flow pattern for the mixing of liquid at least in or on the reaction reservoir and which includes at least one sound wave generation device (15, 115, 215, 315) for the radiation of sound waves into the reaction reservoir (1, 101, 201) or in the direction of the reaction reservoir (301).

22. A device in accordance with claim 21, wherein the metering capillary structure (103) includes at least two predetermined openings (121, 122) which are optionally to be opened and which are arranged along the metering capillary structure.

23. A device for the integrated metering and mixing of small quantities of liquid for the carrying out of the method in accordance with claim 1, comprising:

at least one metering reservoir (3, 103, 203, 223, 303) for a first quantity of liquid;

a reaction reservoir (1, 101, 201, 301) for a second quantity of liquid;

at least one connection structure (11,111, 211, 212, 311) between the at least one metering reservoir and the reaction reservoir, with the connection structure being dimensioned such that when the metering reservoir is completely filled with the first liquid said first liquid does not enter into the reaction reservoir (1, 101, 201, 301) due to its surface tension;

a device (15, 115, 215, 315) for the generation of a flow pattern for the mixing of liquid at least in or on the reaction reservoir and which includes at least one sound wave generation device (15, 115, 215, 315) for the radiation of sound waves into the reaction reservoir (1, 101, 201) or in the direction of the reaction reservoir (301); and at least one filling structure (307) for the filling of the at least one metering reservoir (303) which is connected to the at least one metering reservoir (303) via feeds (308).

24. A device in accordance with claim 23, wherein the feeds (308, 310) include capillary structures.

* * * * *

UNITED STATES PATENT AND TRADEMARK OFFICE

CERTIFICATE OF CORRECTION

PATENT NO. : 8,062,904 B2
APPLICATION NO. : 11/794768
DATED : November 22, 2011
INVENTOR(S) : Christoph Gauer It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 566 days.

Signed and Sealed this
Twentieth Day of March, 2012

David J. Kappos
*Director of the United States Patent and Trademark Office*